(12) United States Patent
Nijsen et al.

(10) Patent No.: US 6,373,068 B1
(45) Date of Patent: Apr. 16, 2002

(54) APPARATUS AND METHOD FOR PREPARING RADIOACTIVE MEDICINES FOR ADMINISTRATION

(75) Inventors: Johannes Franciscus Wilhelmus Nijsen, Hilversum; Alfred Dirk van het Schip, Nieuwegein; Bernard Antoni Zonnenberg, Maarssenbroek, all of (NL)

(73) Assignee: Academisch Ziekenhuis Utrecht, Utrecht (NL)

( * ) Notice: Subject to any disclaimer, the term of this patent is extended or adjusted under 35 U.S.C. 154(b) by 0 days.

(21) Appl. No.: 09/424,624
(22) PCT Filed: May 27, 1998
(86) PCT No.: PCT/NL98/00304
§ 371 Date: Nov. 24, 1999
§ 102(e) Date: Nov. 24, 1999
(87) PCT Pub. No.: WO98/53859
PCT Pub. Date: Dec. 3, 1998

(30) Foreign Application Priority Data

May 27, 1997 (NL) ............................................. 1006135

(51) Int. Cl.[7] ................................................. A61N 5/00
(52) U.S. Cl. ........................... 250/432 PD; 250/432 R; 250/496.1; 250/497.1; 250/436; 250/505.1; 600/3; 600/8; 424/1.11
(58) Field of Search .......................... 250/493.1, 496.1, 250/497.1, 432 PD, 432 R, 436, 505.1; 600/3, 8; 424/1.11, 455

(56) References Cited

U.S. PATENT DOCUMENTS 4,782,231 A 11/1988 Svoboda et al. ...... 250/432 PD
5,395,300 A * 3/1995 Liprie ........................... 600/3

FOREIGN PATENT DOCUMENTS

EP 0587106 4/1994 ........... C07C/51/41

OTHER PUBLICATIONS

Mumper R J et al., Neutron–Activated Holmium–166–Poly (L–Lactic Acid) Microspheres: A Potential Agent for the Internal Radiation Therapy of Hepatic Tumors, Journal of Nuclear Medicine, vol. 32, No. 11, Nov. 1, 1991, pp. 2139–2143.

Mumper, Russell J. et al, "Poly (L–Lactic Acid) Microspheres Containing Neutron–Activatable Holmium—165: A study of the physical characteristics of microspheres before and after irradiation in a nuclear reactor", Pharm. Res., (1992) 9(1), 145–154.

Mumper, Russell J. et al. "Formation and Stability of Lanthanide Complexes and Their Encapsulation into Polymeric Microspheres", J. Phys. Chem. (1992), 96(21), 8626–8631.

(List continued on next page.)

Primary Examiner—Bruce Anderson
Assistant Examiner—Nikita Wells
(74) Attorney, Agent, or Firm—Kinney & Lange, P.A.

(57) ABSTRACT

An irradiation vessel is made from such material and in such form that it can also be used as administration vessel of a medicine contained therein, this medicine first being irradiated with neutrons in a nuclear reactor and subsequently being administered as radioactive medicine to a patient without the medicine having to be moved outside the vessel intermediately. To prevent additional handling operations, with the risk of contamination of the medicine, higher radiation doses to personnel and radioactive contamination of the environment when vessels are used in which the irradiation and administration take place separately, a vessel has been developed which allows a medicine to be irradiated and to be directly administered to the patient thereafter via an external carrier liquid.

15 Claims, 3 Drawing Sheets

OTHER PUBLICATIONS

Figure 1:
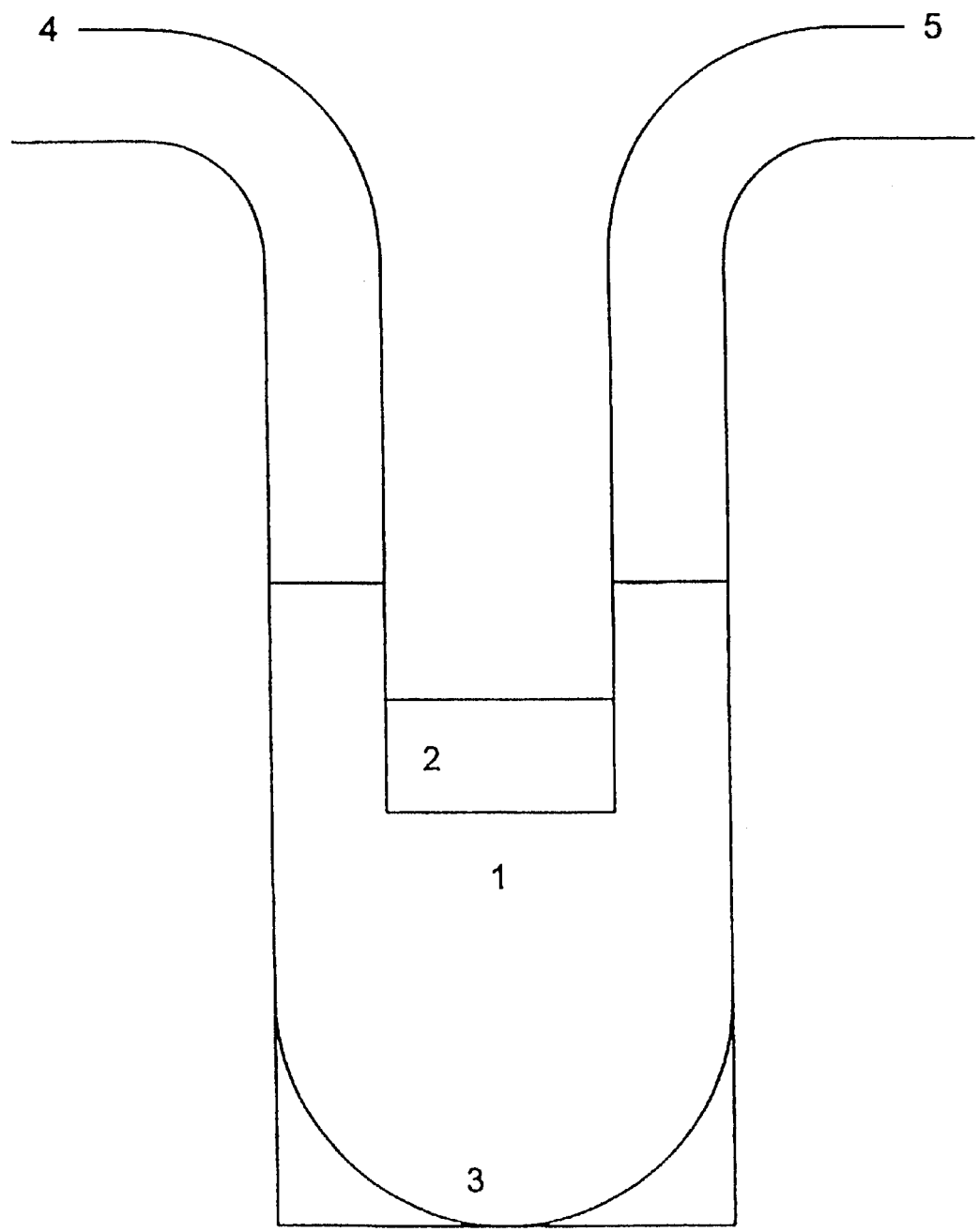

Smith, Suzanne V. et al., "166Dy!dysprosium/'166Ho!holmium in vivo generator", appl. Radiat. Isot. (1995), 46(8), 759–764.

Mumper, Russell J. et al., "Polymeric Microspheres for Radionuclide Synovectomy Containing Neutron–Activated Holmium–166"J. Nucl. Med. (1992), 33(3), 398–402.

Mumper R J et al., "Biodegradable Radiotherapeutic Polyester Microspheres: Optimization and In–Vitro/In Vivo Evaluation", Journal of Controlled Release, vol. 18, No. 3, Apr. 1, 1992, pp. 193–203, see p. 193, col. 1, line 1—col. 2, line 14.

Ma D. et al., Development of the Dysprosium–166 Holmium In–Vivo Generator for Radionuclide Radiotherapy, Journal of Nuclear Medicine, vol. 34, No. sup.5, 1993, p. 231p.

* cited by examiner

APPARATUS AND METHOD FOR PREPARING RADIOACTIVE MEDICINES FOR ADMINISTRATION

The invention relates to a method for preparing radioactive or like medicines for administration. Such method is known from practice.

In the known method, an amount of medicine is introduced into a first container and irradiated therein with neutrons, after which the medicine is introduced into a second container to be sent to an end user. By the end user, for instance a doctor, analyst, laboratory technician or assistant, a dose of the medicine is subsequently transferred into an apparatus whereby it can be administered to a patient.

Separate vessels for irradiating and administering the (radio)active medicine are already used in a standard way.

It has been found that such vessels require many additional operations, in particular for transferring high radioactive material from one vessel to the other. This involves a substantial risk of a dose of radiation to the user in the widest sense (producer of the radioactive medicine, analyst, laboratory technician, etc.), at least of an undesired extra dose of radiation. Moreover, these operations take up extra time and entail a greater risk of contamination of the medicine and radioactive contamination of the environment.

The object of the invention is to provide a method for preparing radioactive or like medicines for administration, wherein the above drawbacks are avoided. To that end, a method according to the invention is characterized by the features of claim 1.

In the most general sense, the invention provides a method for preparing for administration a medicine which is to be shielded from the environment, wherein a vessel is employed which can be used both for irradiation and for administration thereof to a patient, so that the medicine need not be intermediately transferred to another vessel. In this regard, 'medicine' should be understood to comprise at least any means that can be administered to a patient for medicinal or diagnostic purposes. In this context, 'not active', or 'disintegrating sufficiently quickly' should be understood to mean that the material of the vessel preferably disintegrates more quickly than the irradiated medicine, and/or the vessel exhibits an activity-lower than 500 Bq/g preferably within 48 hours.

A method according to the invention offers the advantage that from the vessel in which it is irradiated the medicine can directly be administered to a patient by known means suitable therefor, such as a drip, pump means and the like. Moreover, such method has the advantage that, if desired, for each individual patient a suitable dose with a suitable irradiation can in a separate vessel be prepared for administration, which has advantages in terms of logistics and safety.

The invention further relates to an apparatus for preparing radioactive or like medicines for administration, characterized by the features of claim 6.

The vessel in an apparatus according to the invention is made from such material and in such form that it can also be used as administering vessel of a medicine contained therein, which medicine is first irradiated with neutrons in a nuclear reactor and can subsequently be administered to a patient as radioactive medicine without the medicine having to be taken out of the vessel intermediately.

The vessel preferably comprises at least one coupling connection (for instance Luer Lock) and the vessel is manufactured from a material which at least through neutron irradiation does not become active or disintegrates sufficiently quickly after activation, while, moreover, the vessel can preferably be autoclaved.

In a further embodiment, a vessel according to the invention is further characterized by the features of claim 7.

The separate compartment, separated from the vessel or communicating with the inner space of the vessel via an opening, offers the advantage that a small amount of medicine can be irradiated therein in the same manner as the medicine contained in the inner space of the vessel proper, or that after irradiation, a small amount of irradiated medicine can be received in this compartment. After irradiation, this small amount of medicine can at least partly be removed and checked without the other amount of medicine being affected thereby.

An irradiation/administration vessel according to the invention provides that the medicine can both be irradiated and administered to the patient in an easy and radiation load-reducing manner. For administration, the vessel can entirely be transferred within a shield, so that the radiation coming from the vessel is shielded. Preferably, the vessel is designed so that the radioactive medicine can be fed into a patient by means of an external carrier fluid. In this regard, the vessel is made from material which can hardly be activated, if at all, such as polyethylene, polypropylene, polycarbonate or another synthetic material suitable therefor or quartz glass. The vessel may also be made from a material which, after activation, disintegrates quickly, such as for instance a synthetic material having a fluorine compound such as Teflon.

An apparatus according to the invention can for instance be used as follows.

The vessel is closed during irradiation and before administration. The vessel can be autoclaved or sterilely filled with the medicine to be irradiated. After irradiation, the vessel is sent to the user. Here, a unit with carrier liquid is connected to the vessel and the radioactive medicine is suspended or dissolved in this liquid. After that, the vessel is connected to an administering apparatus which is connected to the patient. The medicine in the vessel is subsequently fed into the patient by the carrier liquid.

The invention further relates to the use of an apparatus according to the invention for preparing a radioactive or like medicine for administration, characterized by the features of claim 20.

Further advantageous embodiments of a method and apparatus according to the invention are given in the subclaims.

Hereinafter, the invention will be specified with reference to three Figures.

Figure 2:
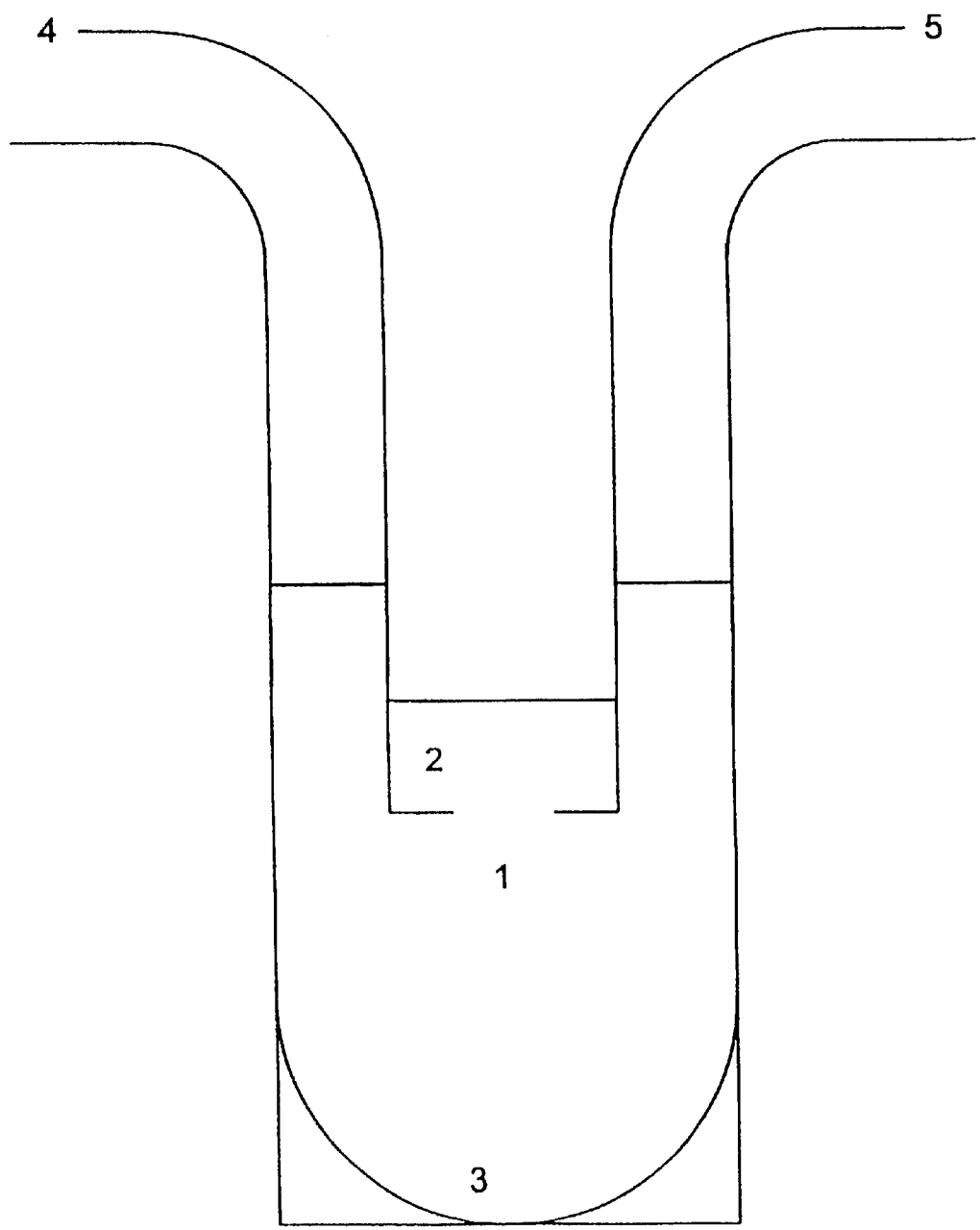
Figure 3:
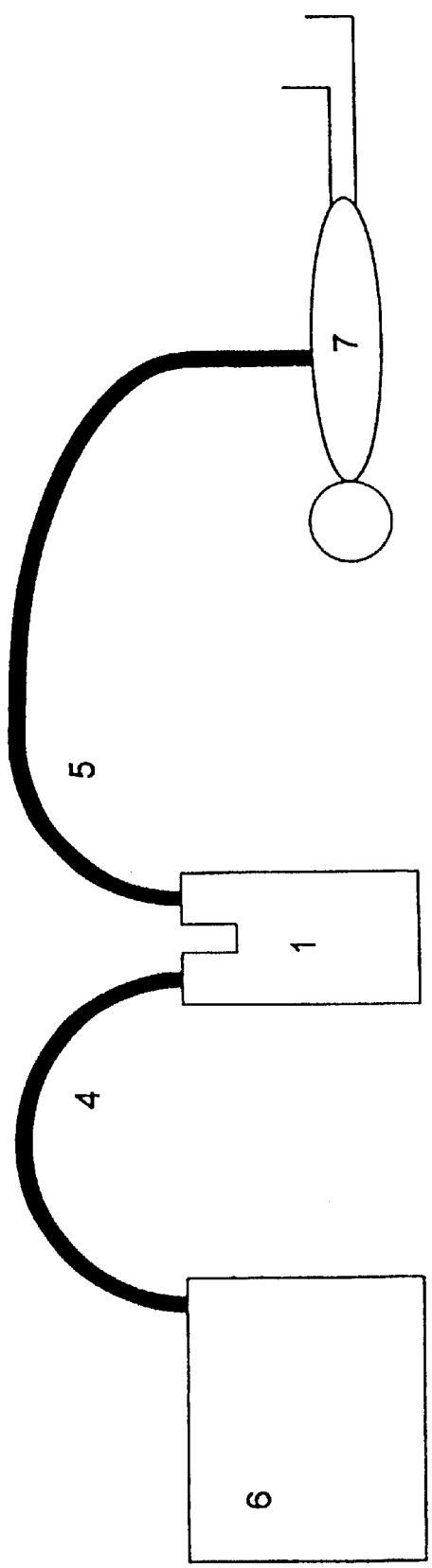

FIGS. 1 and 2 are schematic sectional side elevations of an apparatus according to the invention, FIG. 1 showing a compartment 2 separated from the vessel 1, and FIG. 2 showing a compartment 2 communicating with the vessel 1; and FIG. 3 shows the vessel 1 in connected condition for administering a medicine to a patient 7.

FIGS. 1 and 2 are sectional side elevations of an apparatus according to the invention, comprising a vessel 1, first connecting means 4 and second connecting means 5. The vessel 1 comprises a preferably flowing bottom 3 to obtain an unobstructed flow path between the first and the second connecting means 4, 5. Located on the bottom 3 is the radioactive medicine. The vessel 1 may have different shapes, but is preferably shaped such that a radioactive medicine contained and irradiated therein can readily be suspended or dissolved. The vessel 1 in FIG. 1 contains a separated compartment 2 which can be filled with a part of the medicine. The vessel 1 in FIG. 2 contains a compartment which communicates with the inner space of vessel 1 and which can be filled, after irradiation, with a part of the irradiated medicine. This compartment 2 can be opened, after which at least a portion of the medicine contained therein, also irradiated, can be used for a quality test.

The first and second connecting means 4, 5 are arranged for establishing a liquidtight connection to relatively a unit 6 of a carrier liquid and a connecting hose 5 of an apparatus for administering the suspended or dissolved medicine to a patient 7 as shown in FIG. 3.

An apparatus according to the invention can for instance be used as follows, it being observed that the given values serve as an example only and must not be construed as being limitative.

200 mg holmium-charged Poly Lactic Acid microspheres of 20–40 µm was included in a vessel 1 manufactured from polyethylene, while 10 mg holmium-charged Poly Lactic Acid microspheres of 20–40 µm was included in the compartment 2. The vessel 1 was positioned in an irradiating apparatus of a highflux nuclear reactor and irradiated therein for 1 hour with a neutron flux equal to or higher than $9.10^{12}$ neutrons ($cm^{-2}.s^{-1}$), whereupon the vessel was transferred to a user, where it was connected to an apparatus for administration to a patient having hepatic metastases. The medicine from the compartment 2 was withdrawn therefrom by means of an injection needle and subjected to a quality check.

Subsequently, 25 ml 10 mM phosphate buffered salt pH 7.4 was passed through the vessel 1, into which the medicine was incorporated, whereupon the medicine with the carrier liquid was fed to the patient via an infusion pump.

The vessel 1 is made from such material that neutron activation of vessel 1 in itself does not produce a radiation dose for persons which exceeds the legal standards applying thereto, and that after administration of the medicine to the patient, the vessel 1 can be regarded as non-radioactive waste.

The invention is by no means limited to the embodiments given in the description and the Figures. Many variations thereto are possible. For instance, the vessel may comprise combined first and second connecting means, with all necessary carrier liquid being fed into the vessel or only a portion of the carrier liquid being fed into the vessel, the other carrier liquid being fed along the connecting means such that the medicine is entrained therein through a suction action. Further, the vessel may have a different shape, while means may be provided for obtaining, for instance, turbulence in the vessel for a better suspension of the medicine in a carrier liquid. Further, for the carrier liquid, other administering and supply means may be used than the ones shown. Also, several doses of medicine may be prepared, and an apparatus according to the invention may comprise several vessels that are separate or (to be) interconnected. These and many further variations are understood to fall within the framework of the invention.

What is claimed is:

1. A method for preparing radioactive medicines for administration to a patient, wherein the medicine is introduced into a vessel and irradiated in said vessel, characterized in that said vessel comprises a means for administering the medicine directly from said vessel to a patient, said vessel being manufactured from a material which at least by neutron irradiation does not become active or disintegrates sufficiently quickly after activation.

2. A method according to claim 1, characterized in that a portion of the medicine is included in a separate compartment of the vessel and is removed from said compartment after irradiation for a quality check.

3. A method according to claim 1, characterized in that after irradiation, a portion of the medicine is included in a compartment communicating with the inner space of the vessel via an opening and is removed from said compartment for a quality check.

4. A method according to claim 1, characterized in that after irradiation, a liquid is introduced into the vessel, into which liquid the irradiated medicine is at least substantially incorporated, whereupon the medicine together with the liquid is fed from the vessel to the means for administration to the patient.

5. A method according to claim 4, characterized in that after irradiation, a first connecting opening of the vessel is connected to supply means for the liquid, in particular a suspension liquid, and second connecting means of the vessel are connected to the means for administering the medicine to the patient, the liquid being introduced into the vessel via the first connecting opening, the medicine being incorporated into the liquid in the vessel and subsequently discharged via the second connecting means.

6. An apparatus for preparing radioactive medicines for administration to a patient, comprising a means for containing at least part of said radioactive medicine for irradiation thereof and means for administrating said radioactive medicine to a patient, characterized in that said means for containing at least part of said radioactive medicines is a vessel manufactured from material which at least through neutron irradiation does not become active or, after activation, disintegrates sufficiently quickly, wherein said vessel comprises means for feeding therein a liquid for incorporating said at least part of said radioactive medicine irradiated in said vessel and means for passing said liquid with said at least part of said medicines incorporated therein from said vessel toward a patient.

7. An apparatus according to claim 6, characterized in that a compartment separated from the vessel or communicating with the inner space of the vessel via an opening, is provided for receiving a portion of the medicine that has been or is to be irradiated, means being provided for taking up said portion of the irradiated medicine from the compartment for a quality check thereon without the other amount of irradiated medicine being affected thereby in any way.

8. An apparatus according to claim 6, characterized in that the vessel is made from polyethylene, polypropylene or polycarbonate.

9. An apparatus according to claim 6, characterized in that the vessel is made from quartz glass.

10. An apparatus according to claim 6, characterized in that the vessel is made of polytetrafluorethene or a like compound with fluorene.

11. An apparatus according to claim 6, characterized in that the vessel is also suitable for the irradiation of organic material in addition to inorganic material.

12. An apparatus according to claim 6, characterized in that the vessel is suitable for the irradiation of Poly Lactic Acid microspheres having medicines bound therein.

13. An apparatus according to claim 6, characterized in that the vessel is suitable for the irradiation of Poly Lactic Acid microspheres having holmium acetylacetonate (HoAcAc) bound therein.

14. An apparatus according to claim 6, characterized in that the vessel is suitable for the irradiation of Poly Lactic Acid microspheres having HoAcAc bound therein, wherein as solvent for the Poly Lactic Acid and the HoAcAc dichloromethane is used.

15. Use of an apparatus according to claim 6 for preparing a radioactive medicine for administration, the medicine being irradiated in the apparatus and supplied from the apparatus to an apparatus for the administration thereof to a patient.

* * * * *